(12) United States Patent
Whittle et al.

(10) Patent No.: US 10,195,159 B2
(45) Date of Patent: *Feb. 5, 2019

(54) PROCESSES AND APPARATUS FOR EXTRACTION OF ACTIVE SUBSTANCES AND ENRICHED EXTRACTS FROM NATURAL PRODUCTS

(71) Applicant: GW Pharma Limited, Salisbury (GB)

(72) Inventors: Brian Anthony Whittle, Hornsea (GB); Geoffrey Guy, Glansvilles Wooton (GB); David Victor Downs, Canterbury (GB); David W. Pate, Amsterdam (NL)

(73) Assignee: GW Pharma Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/674,098

(22) Filed: Mar. 31, 2015

(65) Prior Publication Data

US 2016/0038437 A1   Feb. 11, 2016

Related U.S. Application Data

(63) Continuation of application No. 12/618,347, filed on Nov. 13, 2009, now Pat. No. 9,034,395, which is a continuation of application No. 10/476,718, filed as application No. PCT/GB02/02099 on May 7, 2002, now Pat. No. 7,622,140.

(30) Foreign Application Priority Data

May 4, 2001   (GB) .................................. 0111046.9

(51) Int. Cl.
*A61K 31/05* (2006.01)
*B01D 11/02* (2006.01)
*A61K 31/352* (2006.01)
*A61K 36/185* (2006.01)
*B01D 11/00* (2006.01)

(52) U.S. Cl.
CPC ............ *A61K 31/05* (2013.01); *A61K 31/352* (2013.01); *A61K 36/185* (2013.01); *B01D 11/028* (2013.01); *B01D 11/0242* (2013.01); *B01D 11/0273* (2013.01); *B01D 11/0288* (2013.01); *B01D 2011/007* (2013.01)

(58) Field of Classification Search
None
See application file for complete search history.

(56) References Cited

U.S. PATENT DOCUMENTS

| | | | |
|---|---|---|---|
| 3,270,437 A | 9/1966 | Lara et al. | |
| 4,279,824 A * | 7/1981 | McKinney | C07D 311/78 422/164 |
| 5,043,100 A | 8/1991 | Chang et al. | |
| 5,902,587 A | 5/1999 | Carle et al. | |
| 6,095,153 A | 8/2000 | Kessler et al. | |
| 6,403,126 B1 | 6/2002 | Webster et al. | |
| 7,025,992 B2 * | 4/2006 | Whittle | A61K 9/0031 424/435 |
| 7,622,140 B2 * | 11/2009 | Whittle | B01D 11/0242 424/725 |
| 8,790,719 B2 * | 7/2014 | Parolaro | A61K 31/05 424/725 |
| 9,017,737 B2 * | 4/2015 | Kikuchi | A61K 31/05 424/725 |
| 9,034,395 B2 * | 5/2015 | Whittle | B01D 11/0242 424/494 |
| 9,066,920 B2 * | 6/2015 | Whalley | A61K 31/05 |
| 9,474,726 B2 * | 10/2016 | Guy | A61K 31/05 |
| 9,522,123 B2 * | 12/2016 | Whalley | A61K 31/05 |
| 2016/0038437 A1 * | 2/2016 | Whittle | B01D 11/0242 514/733 |

FOREIGN PATENT DOCUMENTS

| | | |
|---|---|---|
| DE | 2920765 C2 | 10/1986 |
| DE | 19654945 C2 | 5/1998 |
| DE | 19804010 A1 | 8/1999 |
| EP | 0053727 A1 | 6/1982 |
| EP | 0796621 A2 | 9/1997 |
| FR | 2 740 706 A1 | 5/1997 |
| GB | 635 121 A | 4/1950 |
| GB | 722 419 A | 1/1955 |
| GB | 851 935 A | 10/1960 |
| GB | 2 026 539 A | 2/1980 |
| GB | 2 377 633 A | 1/2003 |
| GB | 2 400 320 A | 10/2004 |
| JP | 3264091 A | 11/1991 |
| WO | WO 99/11311 A1 | 3/1999 |
| WO | WO 99/53917 A * | 10/1999 |

(Continued)

OTHER PUBLICATIONS

Doorenbos (Annals New York Academy of Sciences (1971), vol. 191, pp. 3-14).*
Carlini (Br. J. Pharmac. (1974), vol. 50, pp. 299-309).*
Repetto (Bulletin on narcotics, (Oct.-Dec. 1976) vol. 28, No. 4, pp. 69-74).*
Rosenkrantz (Toxicology and Applied Pharmacology (1981), vol. 58, pp. 118-131).*
Search Report for GB0409385.2 dated Aug. 11, 2004.
International Search Report and Written Opinion for PCT/GB2002/02099 dated Nov. 25, 2002.

(Continued)

*Primary Examiner* — Susan Hoffman
(74) *Attorney, Agent, or Firm* — Wolf, Greenfield & Sacks, P.C.

(57) ABSTRACT

Processes for preparing extracts of natural products such as plant material, and for preparing purified extracts from crude extracts of natural products, by extraction with hot gas. Apparatus suitable for use in preparing extracts of natural products are also described.

5 Claims, 9 Drawing Sheets

(56) References Cited

FOREIGN PATENT DOCUMENTS

| WO | WO 00/25127 A | 5/2000 |
|---|---|---|
| WO | WO 2004/026802 A1 | 4/2004 |

OTHER PUBLICATIONS

International Preliminary Report on Patentability for PCT/GB2002/02099 dated Sep. 17, 2003.
[No Author Listed] Cannabis L. Vascular plants of Russia and adjacent countries as of Oct. 26, 1996. Int Org Plant Info—Provisional GPC. USDA Plants Database. Generated Jan. 15, 1997.
[No Author Listed] Humulus. Vascular plants of Russia and adjacent countries as of Oct. 26, 1996. Int Org Plant Info—Provisional GPC. USDA Plants Database. Generated Jan. 15, 1997.
Basile et al., Extraction of rosemary by superheated water. Am Chem Soc. 1998;46(12):5205-9.
Lemberkovics et al., Contributions to the essential oil composition of the flowers and leaves of cannabis sativa L. Planta Medica. 1979;36(3):271-2.
Sashida et al.,. Microextraction of volatile constituents using gasified-solvent flow. Yakugaku Zasshi. 1990;110(5): 321-4.
The United Kingdom Parliament, Select Committee on Science and Technology Ninth Report (1998) at http://www.parliament.the-stationery-office.co.uk/pa/ld199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.
Search Report for GB 0210403.2 dated Oct. 15, 2002.
Ruppel et al., Cannabis Analysis: Potency Testing Identification and Quantification of THC and CBD by GC/FID and GC/MS. PerkinElmer: 6 pages. Last accessed from <https://www.perkinelmer.com/lab-solutions/resources/docs/APP_Cannabis-Analysis-Potency-Testing-Identifification-and-Quantification-011841B_01.pdf> on Dec. 14, 2016.

* cited by examiner

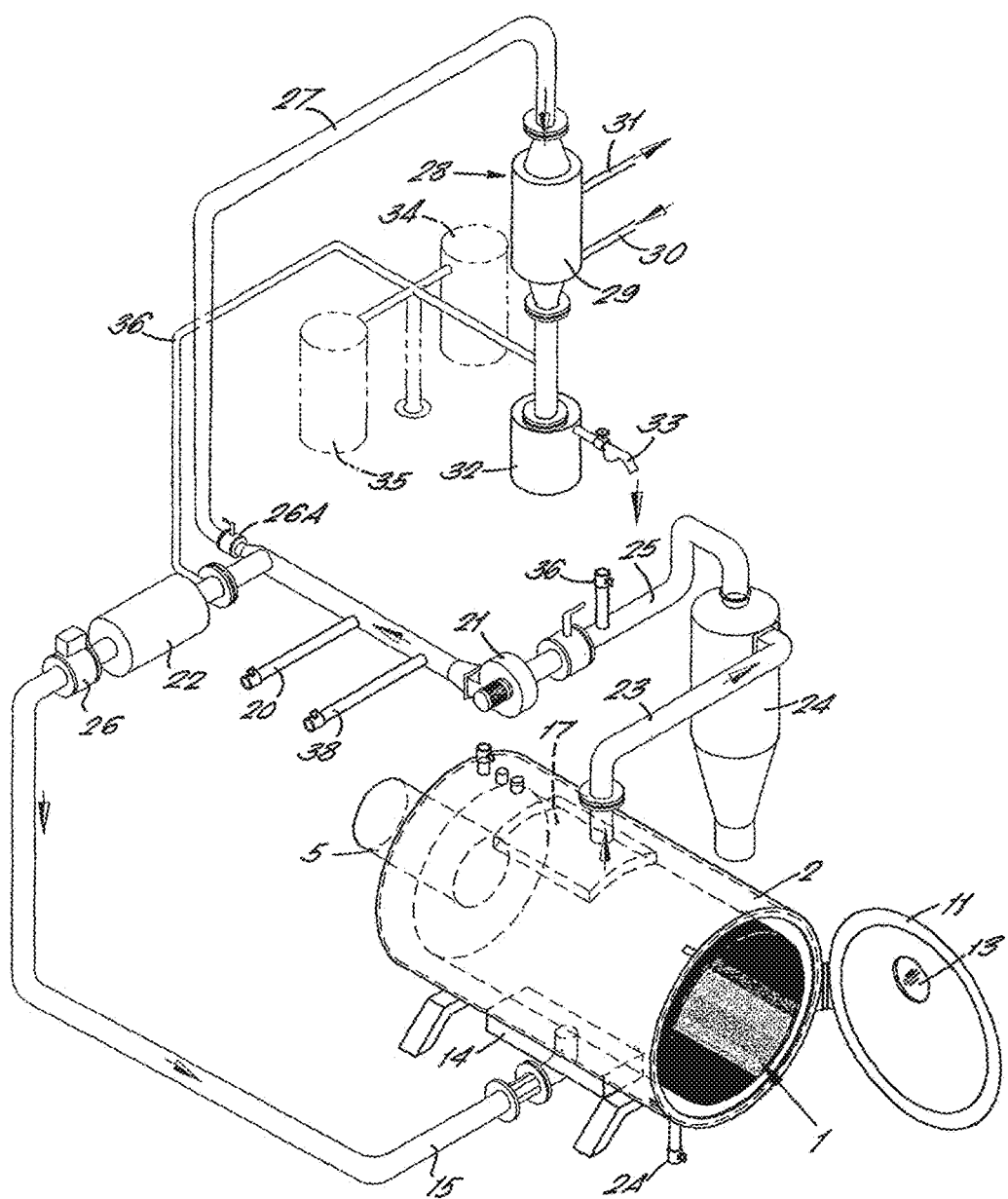

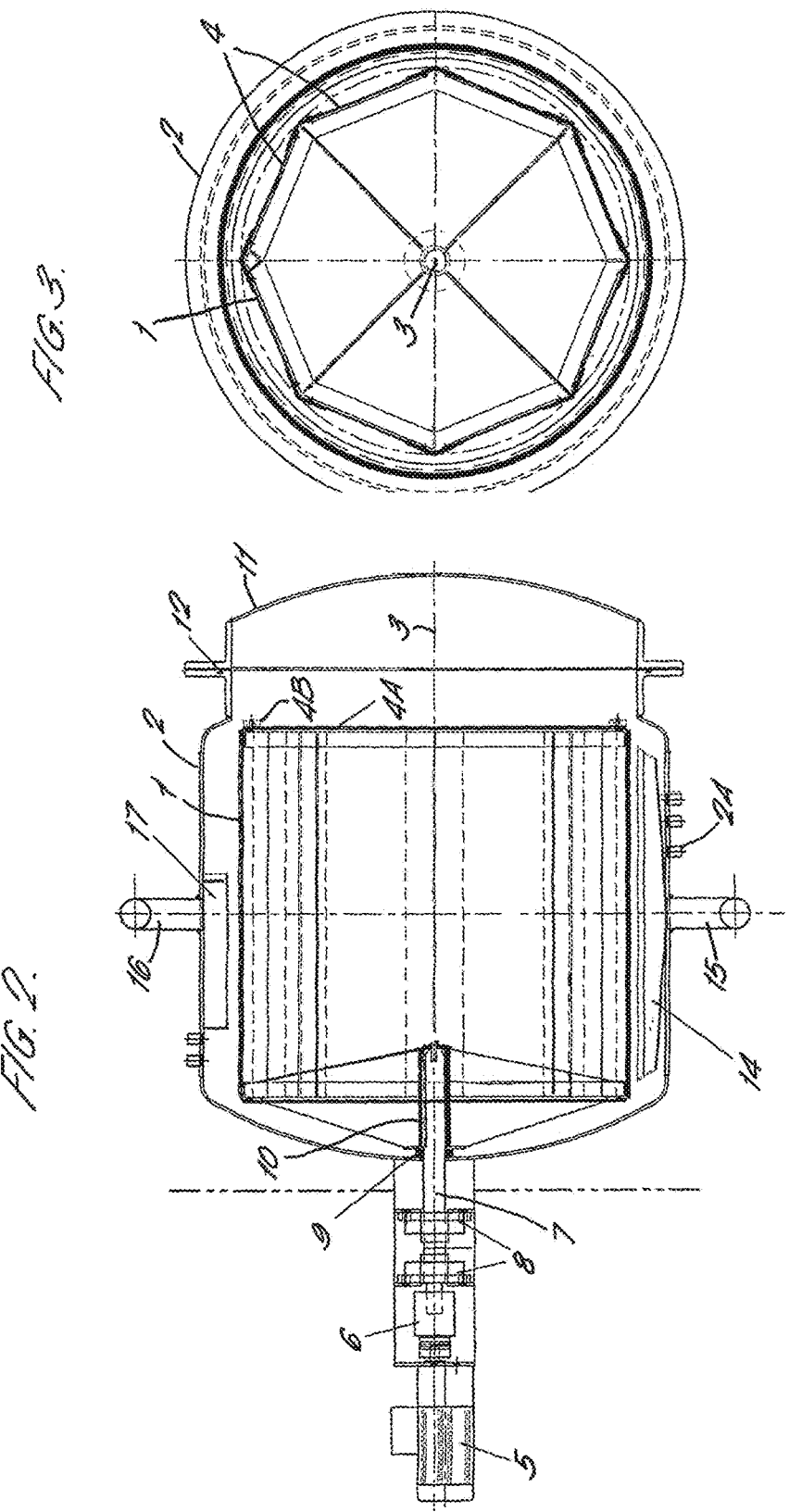

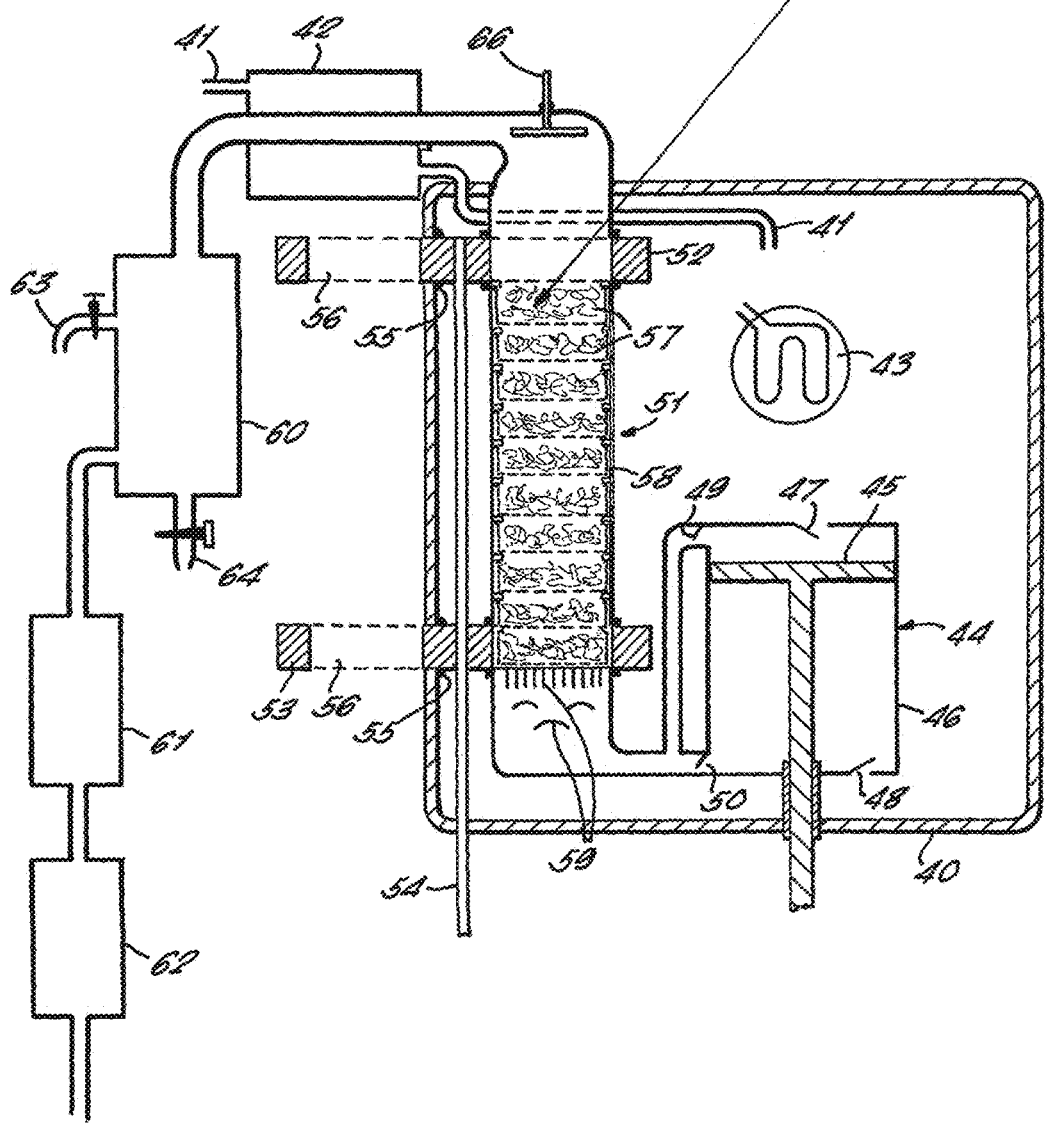

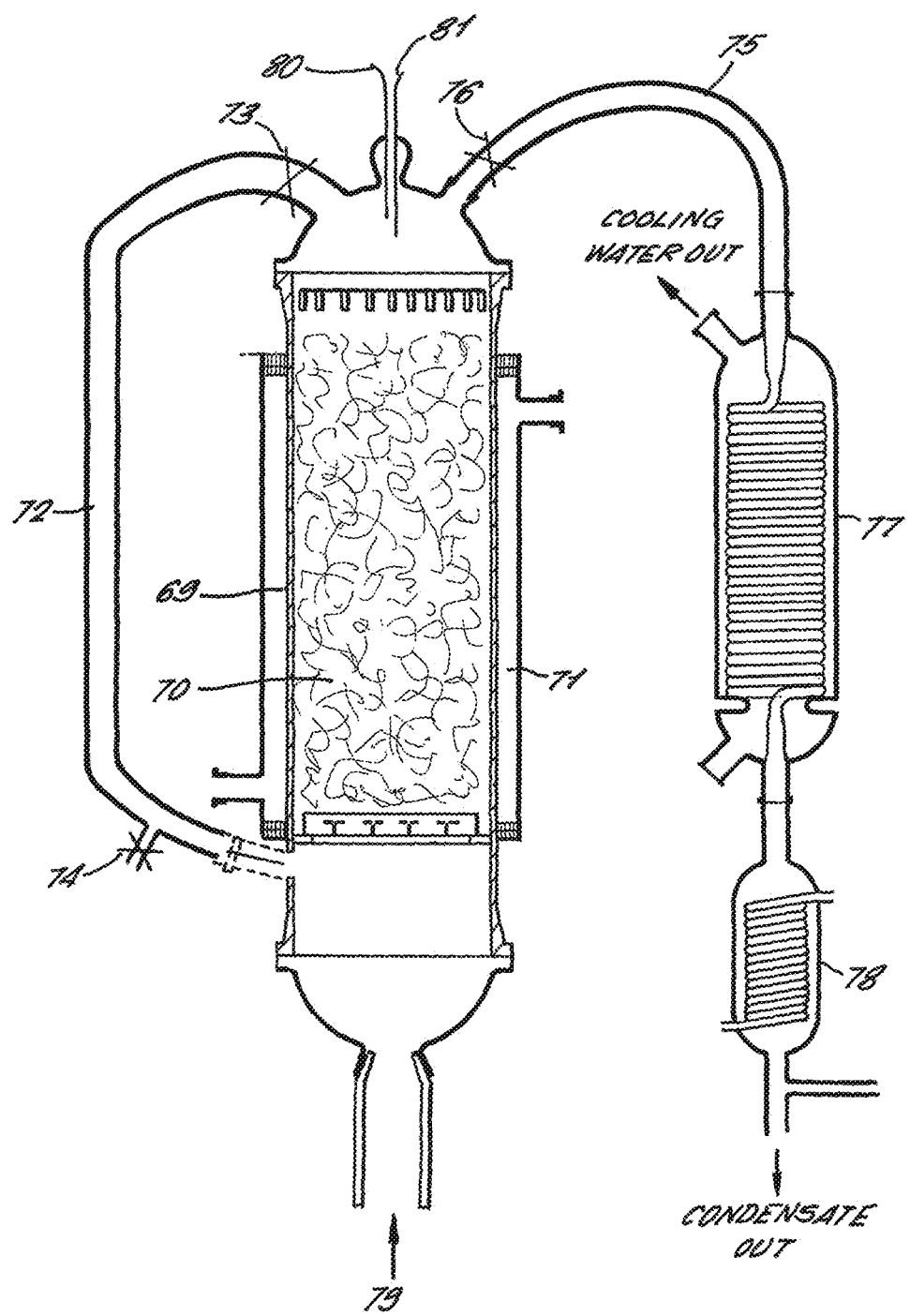

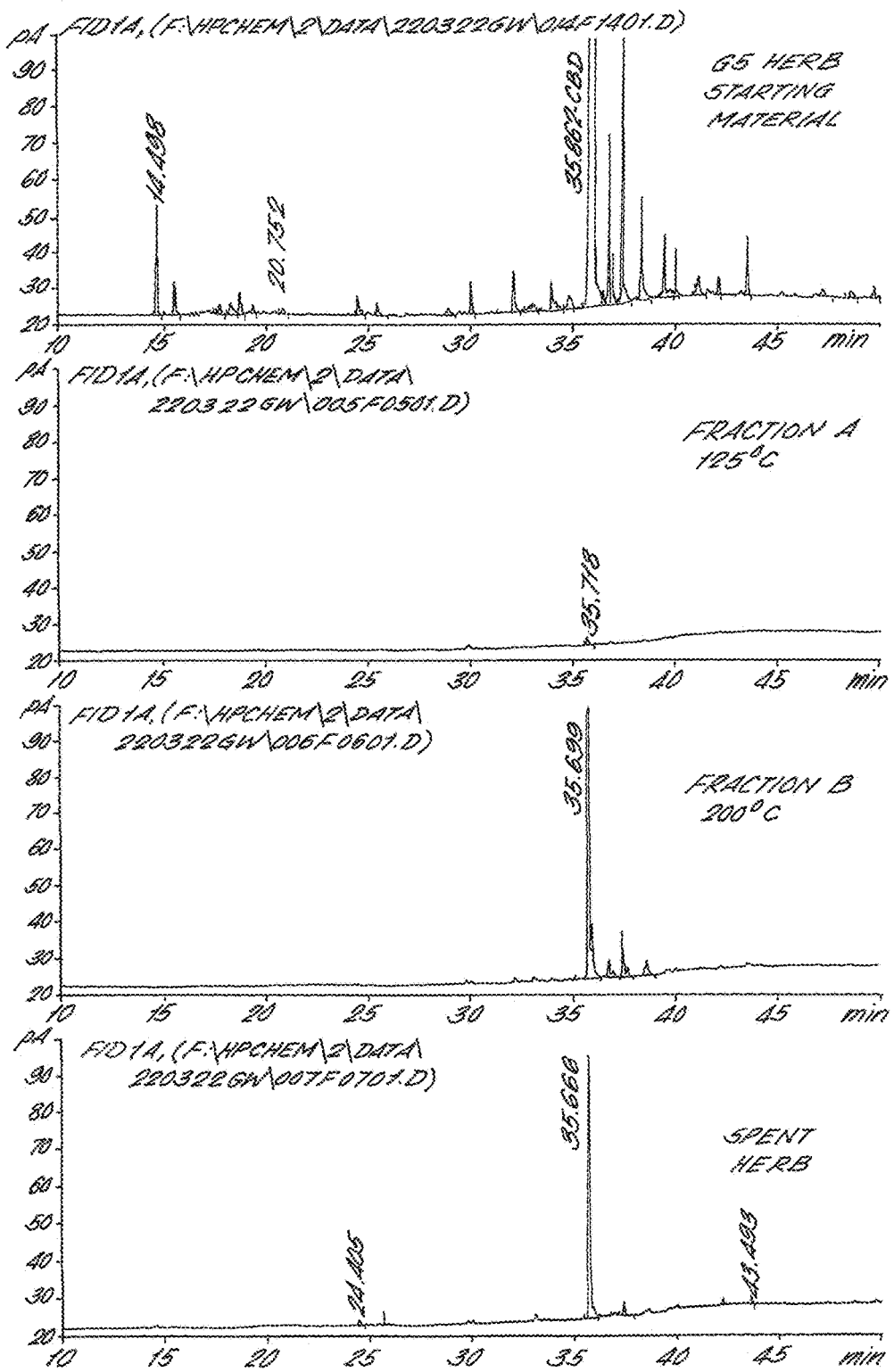

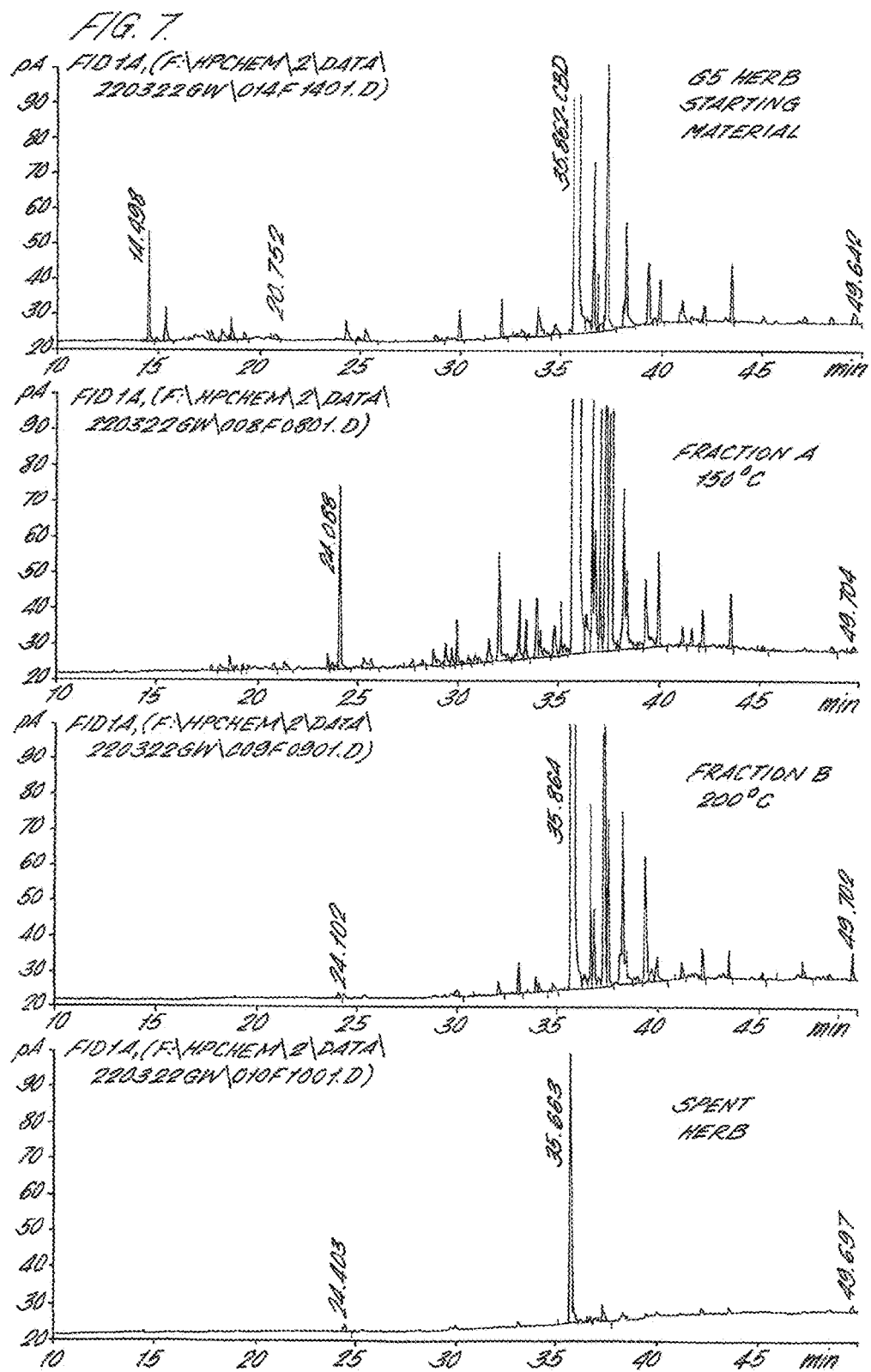

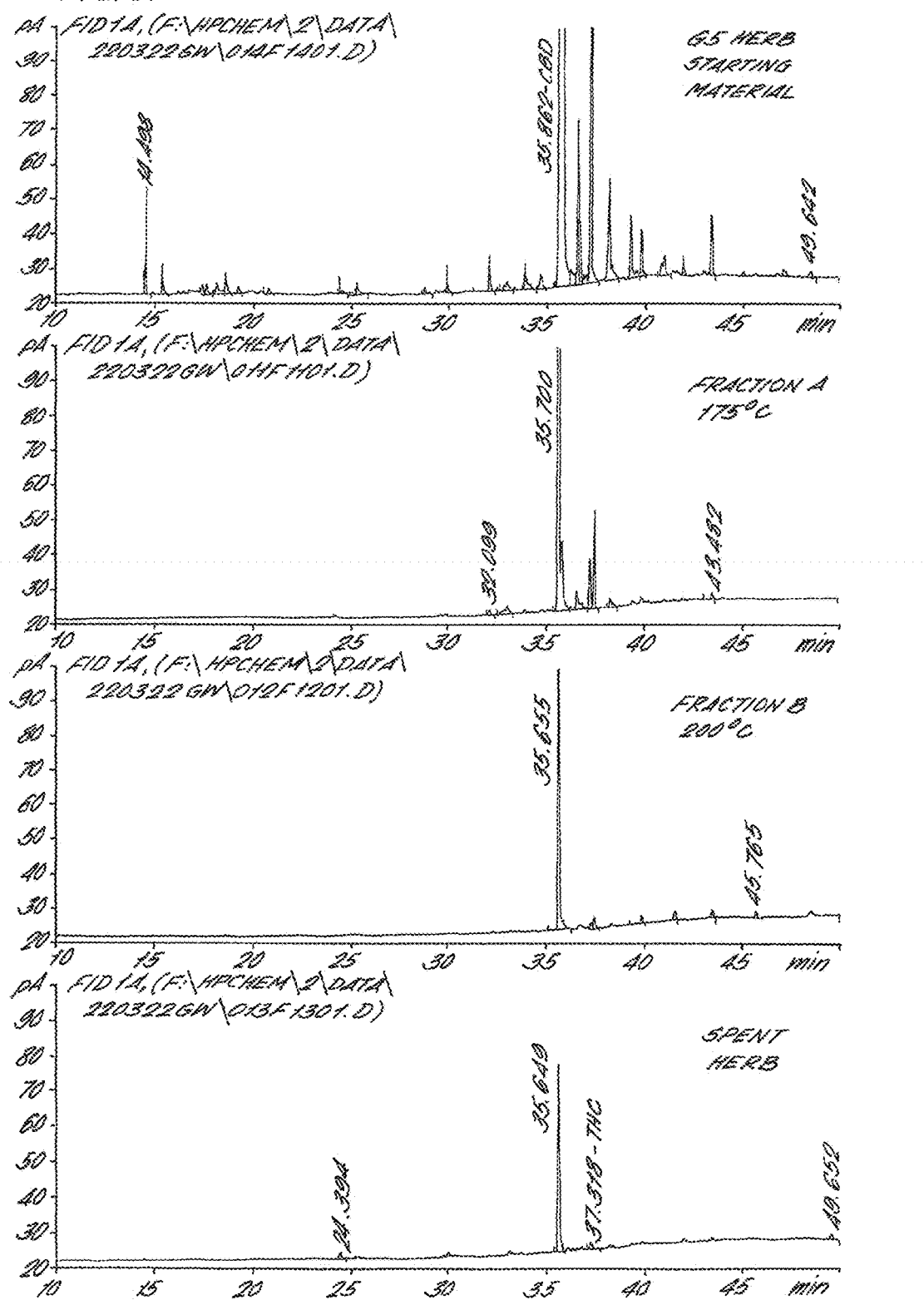

PROCESSES AND APPARATUS FOR EXTRACTION OF ACTIVE SUBSTANCES AND ENRICHED EXTRACTS FROM NATURAL PRODUCTS

RELATED APPLICATIONS

This application is a continuation application of U.S. patent application Ser. No. 12/618,347, filed Nov. 13, 2009, now U.S. Pat. No. 9,034,395, which is a continuation of U.S. patent application Ser. No. 10/476,718, filed Nov. 4, 2003, now U.S. Pat. No. 7,622,140, which is a national stage filing under 35 U.S.C. § 371 of international application PCT/GB2002/002099, filed May 7, 2002, which was published under PCT Article 21(2) in English, the entire contents of each of which are incorporated herein by reference.

FIELD OF THE INVENTION

The present invention relates to processes for preparing extracts of natural products, such as plant material, and for preparing purified extracts from crude extracts of natural products by extraction with hot gas, and also to apparatus suitable for use in preparing extracts of natural products.

BACKGROUND TO THE INVENTION

The therapeutic activity of plant medicines is attributed to the active constituents which they contain. In some cases the intrinsic activity of natural products has been linked to specific chemical species, but in other cases the activity of the plant medicine is considered to be due to a combination of constituents acting in concert. In most plant materials the active constituent is present in varying proportions. For example, vincristine is an alkaloid present in the aerial parts of *Vinca roseaea* at concentrations of less than 0.1% of the dried biomass. In the case of *cannabis* resin, the concentration of active constituent may be more than 60% w/w of resin (hashish). Whatever the concentration in biomass, it is convenient to extract specific constituents, or produce an enriched extract, which can be then formulated into conventional dosage forms for ease of administration.

Methods of extraction which have been used to separate constituents of plant medicines and to produce enriched extracts include maceration, decoction, and extraction with aqueous and non-aqueous solvents, distillation and sublimation.

Maceration (also known as simple maceration) is defined as the extraction of a drug in a solvent with daily shaking or stirring at room temperature. After a defined period the spent, solid material is separated from the solution (macerate). Variation on the method includes agitation of the macerate and the use of temperatures up to approximately 50° C. The method was formerly used for the preparation of tinctures and extracts from low-density plant *materia medica*, using various strengths of ethanol as the extraction solvent.

Decoction has been used since antiquity for the preparation of traditional medicines. In traditional Chinese medicine it is customary to place the quantity of herbs required for one day's treatment into a vessel to which hot or boiling water is added. The vessel is then raised to boiling point and allowed to simmer for 1½ hours (sometimes longer). The decoction so produced is allowed to cool, separated from solid particles, and the decoction is used as the dosage form for oral administration.

Maceration and decoction rely on a short diffusion path. Inactive constituents such as lecithins, flavinoids, glycosides and sugars may act to solubilise constituents which, in the pure state, are really soluble in the solvent. A disadvantage of maceration and decoction with water or low concentrations of ethanol is that a large quantity of inert material (ballast) that does not have therapeutic value is extracted. Ballast may consist of plant cell constituents including, but not limited to, fats, waxes, carbohydrates, proteins and sugars. This may contribute to microbiological spoilage if the product is not used promptly. If dried, the extracts so produced tend to be hygroscopic and difficult to formulate. The ballast may also affect the way in which the active constituents are absorbed from the finished dosage form.

Maceration and decoction are still widely used in situations where the balance of convenience inherent in the low technology involved outweighs the lack of precision in such technology in the context of pharmaceutical production. In the case of macerates and percolates, solvents may be removed by evaporation at temperatures below 100° C. and preferably below 60° C.

A wide range of processes based on the use of non-aqueous solvents to extract the constituents from plants have been used in the prior art. The solvents employed may be miscible with water or water immiscible and vary in solvent power according to the concept of E°, which is familiar in the context of chromatography.

Traditionally, ethyl alcohol in various concentrations has been used to extract active substances from plant materials. Tinctures are alcoholic solutions produced in this way and tinctures of plant materials are described in all major pharmacopoeias. Where the final concentration of alcohol is greater than approximately 20% by volume, the tincture remains microbiologically stable and such tinctures have been widely used in compounding prescriptions. Ethanol extracts substances such as glycosides, flavinoids and alkaloid salts which are examples of classes of compound known to be biologically active. It also extracts considerable amounts of plant pigment, such as chlorophyll and carotenoids. By using higher alcoholic strengths lipid-soluble material may be extracted. Tinctures contain less ballast than macerates or decoctions, but are still complex mixtures of plant constituents. Where the presence of alcohol is not required the tincture can be evaporated to produce extracts. All pharmacopoeias contain liquid and solid extracts produced in this way.

Lipid solvents with a high E° value have been used to extract lipid soluble constituents from biomass. Examples are chlorinated solvents such as dichloromethane, chloroform and carbontetrachloride, hexane, ether, fluorinated hydrocarbons and supercritical fluid extraction with agents such as carbon dioxide.

Chlorinated solvents are no longer used commercially for extraction of plant biomass because they are themselves toxic and for pharmaceutical use the solvent must be removed. They are, however, reactive and can also result in the production of compounds which have been shown to be genotoxic—and may even be carcinogenic. Hexane and other petroleum-based solvents have a high E° value and good solvent activity, but they must be completely removed from the end product and also carry with them risk of fire and explosion.

Extraction with supercritical fluid $CO_2$ has been used to remove active constituents from foods such as caffeine from coffee beans, and humulene and other flavours from hops (*Humulus lupulus*). The process allows for manipulation of E° value by variation of pressure, temperature and by the addition of accessory solvents (modifiers) such as alcohols.

A characteristic of all non-aqueous solvent methods of extraction is that they all, to a greater or lesser degree, remove lipid soluble inactive material or ballast from plant material. The ballast may consist of plant cell constituents including but not limited to fats, waxes, carbohydrates, proteins and sugars. The presence of these substances results in botanical extracts which may be hygroscopic, difficult to reduce to a powder and generally intractable as starting materials for pharmaceutical preparations. The presence of ballast may also limit the shelf-life of pharmaceutical products formulated from such extracts.

Some elements of ballast can be removed by an additional step post-extraction referred to as "winterisation", which involves making a concentrated solution of the extract and cooling it to a temperature at which a proportion of waxes and lipid components may be precipitated, typically −20° C.

Partially purified plant extracts may be further purified by chromatographic separation. High performance liquid chromatography (HPLC) is an excellent analytical technique for determination and assay of constituents and can be used in preparative mode to produce pilot quantities of concentrated fractions and individual components, provided that the required reference standards are available. However, HPLC is subject to limitations of scale as a production technique and there remains a need for alternative methods of separation which can be used to produce production-scale quantities of plant extracts of sufficient quality for formulation into pharmaceutical dosage forms.

Distillation and sublimation have been used to separate components of plant medicines which have boiling points at or around the temperature at which water boils at atmospheric pressure (100° C.). Separation by distillation is a physical process widely used in the preparation of essential oils.

GB 635,121 describes a process for the preparation of extracts from aromatic plants by distillation with the help of a hot gas, preferably under high vacuum.

WO 99/11311 describes a vaporizer for inhalation and a method for the extraction of active ingredients from a crude natural product. This method utilizes an ascending stream of hot air, or a heated inert gas stream, to volatilize components from the natural product. The resultant vapour may then be inhaled by a user, for example to provide therapeutic benefit.

The present inventors have now determined that useful separation of certain plant constituents, which are not considered to be volatile at ambient temperatures, can be effected by extraction with a gas heated to higher temperatures than those traditionally used in distillation. Accordingly, they have developed a process for the preparation of extracts from natural products which avoids many of the disadvantages of the prior art and provides additional technical advantages, particularly in the extraction of pharmacologically active components from plant material.

SUMMARY OF THE INVENTION

In accordance with a first aspect of the invention there is provided a process for preparing an extract from a natural product which comprises contacting the natural product with a heated gas at a temperature which is greater than 100° C. and sufficient to volatilise one or more constituents of the natural product but does not cause pyrolysis of the natural product thereby volatising one or more constituents of the natural product to form a vapour, and condensing the vapour to form an extract.

In accordance with a second aspect of the invention there is provided a process for preparing an extract from a natural product which comprises:
providing a primary solvent extract of the natural product;
contacting the primary solvent extract with a heated gas thereby volatilising one or more
constituents of the primary solvent extract to form a vapour;
condensing the vapour; and
collecting the condensate in one or more fractions.

According to a further aspect of the invention there is provided an apparatus for extracting useful substances from natural products, the apparatus comprising a receptacle for receiving the natural product, a blower to blow gas through the receptacle, a heater for heating the gas blown through the receptacle, a condenser to condense the vapour from the receptacle, and a means for collecting the useful substances in the condensed liquid.

BRIEF DESCRIPTION OF THE DRAWINGS

The invention will be further understood with reference to the drawings, in which:

FIG. 1 is a schematic diagram of a first apparatus in accordance with the present invention;

FIG. 2 is a cross-section through the rotatable drum of FIG. 1;

FIG. 3 is a section through the drum in a plane perpendicular to the axis of rotation;

FIG. 4 is a schematic diagram of a second apparatus; and

FIG. 4A shows the detail of a basket used in FIG. 4.

FIG. 5 is a schematic diagram of an apparatus suitable for carrying out the solvent extract purification process of the invention.

FIGS. 6-10 are gas chromatogram traces showing the composition of fractions volatilized and condensed from *cannabis* botanical raw material at various temperatures, in comparison with the starting raw material and spent herb.

DETAILED DESCRIPTION OF THE INVENTION

Figure 9:
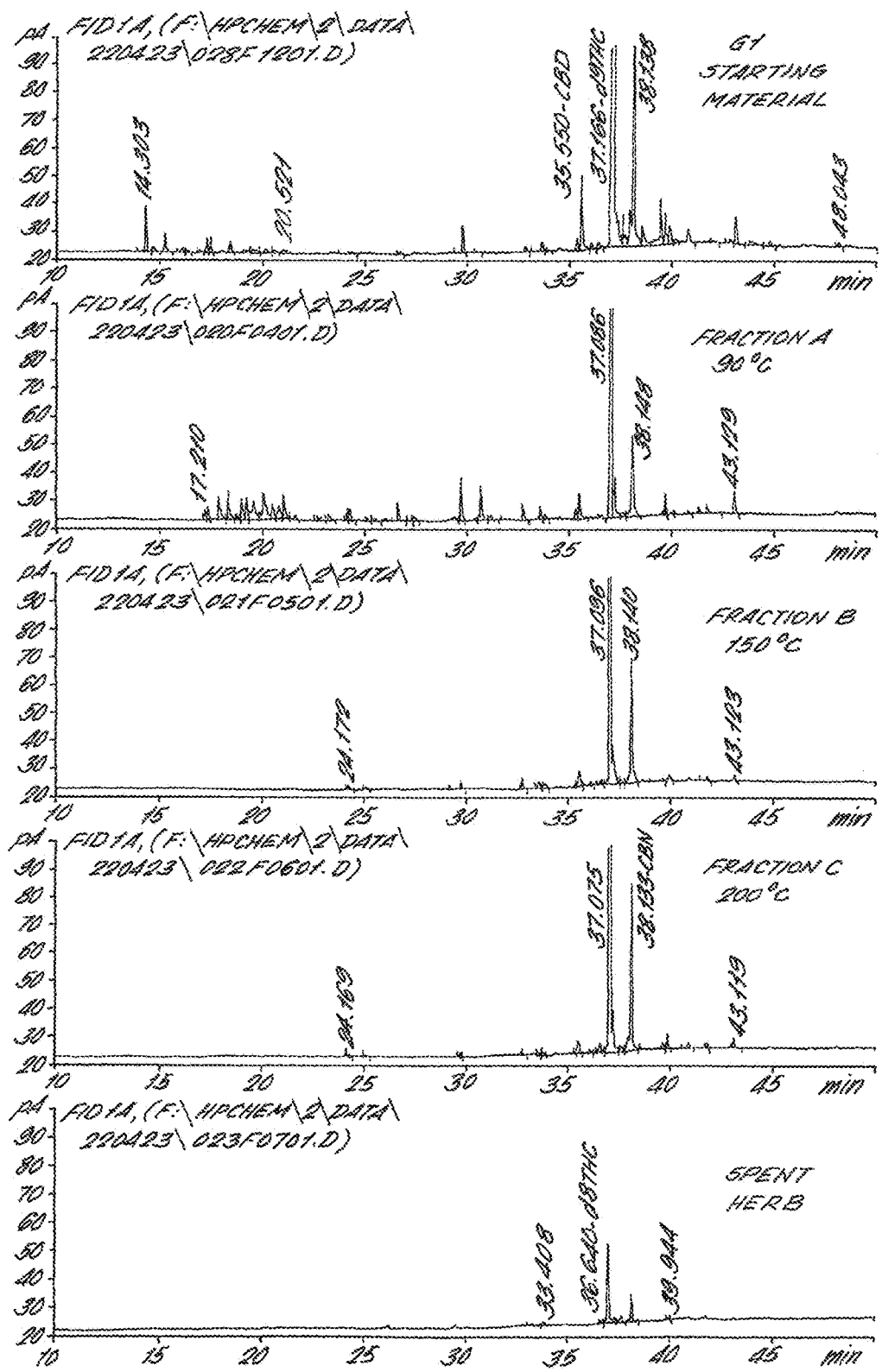

The process according to the first aspect of the invention combines a distillation step in which the natural product is contacted with a hot gas, resulting in volatilisation of one or more constituents of the product to form a vapour, with a condensation step in which the vapour is condensed to form an extract.

If required, the process may further include a step of removing particulate matter from the vapour prior to the condensation step.

The process exhibits unexpected efficiency and selectivity as compared to prior art methods of solvent extraction, particularly in relation to the isolation of cannabinoid-rich fractions from *cannabis* plant material (as illustrated in the accompanying examples).

Contact between the natural product and the heated gas is advantageously achieved by "gas washing" the product. This involves continuous agitation of the product in a stream of the heated gas.

The process may be operated continuously and as such is particularly suitable for use in large scale commercial production of extracts from natural products.

As illustrated in the accompanying Examples, the process of the invention can produce extracts containing minimal ballast which are suitable for direct formulation into standard pharmaceutical dosage forms, i.e. tablets, capsules, sprays, liquid formulations etc.

The condensed extract may be a homogeneous liquid but may, depending on the nature of the starting material, form a mixture of oily and aqueous components. In the latter case, the apparatus used for carrying out the process may include further means for separating the extract into fractions by passing vapour into a condenser with a fractionating column. This type of condenser is commercially available and contains baffle plates or other packing and multiple collection ports for separation of fractions having different boiling points.

The extraction process of the invention is particularly preferred for preparing extracts from plant material. The term "plant material" encompasses whole plants and also parts thereof which contain the principal medically active constituents, for example the aerial parts of the plant or isolated leaves, stems, flowering heads, fruits or roots. The extraction process may be carried out starting from freshly harvested plant material, plant material which has previously been dried by removal of water or plant material which has been subjected to some other pre-treatment step, for example to effect a chemical change in constituents of the plant material.

When using freshly harvested plant material, for example plant material which is still green, the process may advantageously include a pre-treatment step in which the plant material is contacted with a stream of heated gas at a temperature which is sufficient to dry the plant material, by removal of water vapour therefrom. After this initial pre-treatment step the temperature of the heated gas may be increased to a temperature which permits volatilisation of constituents of the plant material.

The precise temperature of the gas used to volatilise constituents of the natural product may vary dependent on the nature of the natural product and on the nature of the constituents it is desired to extract using the process. However, the temperature is always be above 100° C. (during at least a part of the extraction process) and is selected not to cause substantial pyrolysis of the natural product. Typical temperatures will be in the range of from 150 to 450° C. The extraction is preferably carried out at or above atmospheric pressure.

The temperature may be varied over the course of the extraction process. In one embodiment a profile of two or more discrete temperatures may be used, at least one of which is above 100° C. and selected not to cause substantial pyrolysis of the natural product. Most preferably the temperature of the heated gas will be increased at each of the discrete steps. In a further embodiment the temperature of the heated gas could be continuously increased or ramped. The use of heated gas at two or more discrete temperatures may enable components of the natural products to be volatilised and condensed as separate fractions.

Suitable "heated gases" for use in the process include hot air. However, the use of hot air can result in oxidative degradation of constituents of the extract produced during the extraction process. This problem can be avoided with the use of a "non-oxidising gas". By the term "non-oxidising gas" is meant a gas which causes less oxidation of the extract produced from the natural product than air under equivalent process conditions. A preferred type of "non-oxidising" gas is dry steam i.e. steam at a temperature above 100° C. which is free of condensed water vapour.

Further protection against the effects of oxidation can be achieved with the use of a "reducing gas". Suitable reducing gases include gases containing a pharmaceutically acceptable anti-oxidant, sulphur dioxide mixed with steam, carbon dioxide and inert gases such as, for example, nitrogen, helium and argon. The use of a reducing gas is particularly advantageous in relation to the extraction of cannabinoid-rich fractions from *cannabis* plant material, as discussed below.

In one particular embodiment, useful for preparation of extracts from freshly harvested or "wet" plant material, a reducing gas may be produced in situ by addition of a solution of sodium metabisulphite to a stream of heated steam. When mixed with wet plant material, sodium metabisulphite reacts to produce sulphur dioxide which provides an antioxidant environment, minimising the extent of oxidation of the extract. The quantity of sodium metabisulphite added to the steam is typically sufficient to give 10-500 parts of sulphur dioxide per million parts of wet plant material.

Surprisingly, it has been found that application of temperatures greater than those used for steam distillation can also speed the conversion of inactive constituents of natural products into compounds which are biologically active and can be separated in high purity by heating and condensation under defined conditions. For example, the principal active constituents of *Cannabis saliva* and *Cannabis indica* are the cannabinoids—principally tetrahydrocannabinol (THC) and cannabidol (CBD). Cannabinoids such as cannabigerol (CBG), cannabichromene (CHC) and other cannabinoids are present in small quantities in harvested *cannabis* plants. The majority of cannabinoids are present in the plant as the corresponding carboxylic acids. The carboxylic acids themselves have little or no biological activity and in the production of cannabinoids for medicinal use it is necessary to convert the cannabinoid acids into free cannabinoids before extracting with solvents or other procedures. Thus when preparing extracts of *cannabis* by extraction with ethanol or supercritical $CO_2$ it is necessary to preheat the *cannabis* in order to decarboxylate the cannabinoid acids to free cannabinoids.

Surprisingly, it has been found that by contacting *cannabis* biomass with gas at a temperature of 105-450° C., and particularly in the range 105-225° C., for a suitable period of time, the carboxylic acids are converted into free cannabinoids which are vaporised, and can be condensed. The process of the invention can therefore avoid the need for a separate decarboxylation step, since extraction of *cannabis* with heated gas at a temperature of 105-450° C., and preferably in the range 105-225° C., results in decarboxylation and vaporisation of the active cannabinoids in a single step. The process of the invention is particularly advantageous for preparing extracts of *cannabis* for this reason. The rate of decarboxylation is a product of temperature and time. At 145° C. 95% of cannabinoid acid is decarboxylated in approximately 30 minutes. Lower temperatures may require a longer incubation time and higher temperatures a shorter incubation time to achieve the same degree of decarboxylation. Again this process is preferably carried out at or above atmospheric pressure.

Preferred temperatures and times to achieve optimum decarboxylation may vary according to nature of the cannabinoids which it is desired to extract from the *cannabis* plant material. Chemovars of *cannabis* have been produced which express a high proportion (typically >80% and more preferably >90%) of their total cannabinoid content as either THC or CBD. For convenience, these chemovars are referred to as the "high THC" and "high CBD" chemovars, respectively. In the case of "high CBD" plants, preferred time/temperature profiles to achieve complete decarboxylation are 120° C. for 1 hour or 140° C. for 30 mins. For "high THC" plants it is preferred to use a lower temperature in order to avoid thermal oxidation of $\Delta^9$-THC to CBN and thermal isomerisation of $\Delta^9$-THC to $\Delta^8$-THC. Therefore preferred time/temperature profiles are 105° C. for 1-2 hours or 120° C. for 30-60 mins. For both high CBD and high THC chemovars higher temperatures may be used in order to prepare extracts which are substantially free of volatile ballast components, for example terpenes, as discussed below.

A further surprising advantage of the process of the invention in relation to the isolation of cannabinoid-rich fractions from *cannabis* plants is that the condensate so produced contains the free cannabinoids in a high degree of purity, substantially free from waxes, sterols and other lipid-soluble components which characterise solvent extracts. Table 1 shows the percentage purity of the extract which is produced with the equipment described in the attached diagrams, according to the process described in the accompanying examples. For comparison purposes Table 1 also shows the content of free cannabinoid and the corresponding carboxylic acids in extracts produced by alcoholic extraction and extraction with supercritical carbon dioxide. The table also shows the percentage of ballast which is extracted by these methods. It can be seen that the extraction process of the invention results in an extract which is substantially free of ballast. This extract is of sufficient quality to be processed directly into pharmaceutical dosage forms. In contrast, *cannabis* extracts prepared by extraction with ethanol or supercritical $CO_2$ contain a large proportion of ballast. For example, whilst $CO_2$ extraction is relatively selective, typically yielding an extract with a cannabinoid content of approximately 70% w/w, a range of non-cannabinoid ballast is also present. The process of the invention exhibits markedly increased selectivity for extraction of cannabinoids.

Most of the ballast present in *cannabis* plant material is involatile material. The process of the invention is efficient in separating the desired active cannabinoids from this involatile ballast, since the vast majority of this involatile ballast is simply not volatilized during the hot gas extraction procedure. Thus, removal of waxy ballast material may be unnecessary, or at least rendered easier than with a solvent extract. The other major ballast component is a volatile terpene-rich fraction. An unknown component of this terpene-rich fraction is suspected to be the cause of stability problems in solvent extracts of *cannabis* plant material prepared using supercritical $CO_2$ extraction. Hence, it is highly desirable to remove the volatile terpene-rich fraction.

Using the process of the invention it is possible to collect a cannabinoid-rich fraction which is substantially free of volatile terpenes and wherein the majority of the cannabinoids are present in the decarboxylated neutral form using a single-step temperature profile. This has obvious advantages in comparison to, for example, extraction with $CO_2$ or ethanol in that there is no need for a separate decarboxylation step prior to extraction or for a separate "winterisation" step to remove ballast. Furthermore, the extract is substantially free of volatile terpenes which may cause stability problems. As illustrated in the accompanying examples, for "high CBD" material a single temperature step in the range of 175-200° C. may result in the isolation of a cannabinoid-rich fraction which is substantially free of terpenes. At these temperatures terpenes are volatilised along with the cannabinoid-rich fraction but are not condensed, and are thus lost from the system. In the case of "high THC" material it is preferred to use a lower temperature in order to avoid thermal oxidation of $\Delta^9$-THC to CBN or thermal isomerisation of $\Delta^9$-THC to $\Delta^8$-THC. Temperatures in the range 130-175° C. are preferred. The skilled reader will, however, appreciate that the optimum temperature may vary depending on the characteristics of the apparatus used to carry out the process, for example the amount of raw material processed in each charge, time of contact with the extracting gas and also the conditions used for condensation of the volatilised components. Thus, for any given system conditions of extraction temperature and time should be optimised empirically.

The terpene-rich fraction isolated from *cannabis* raw material may itself have a commercial value as a "waste" product. Hence, it may be advantageous to split the volatile components into terpene-rich and cannabinoid-rich fractions which are condensed and collected separately. This may be achieved by use of a multi-step temperature profile, using at least two discrete temperatures. Since the terpene-rich fraction is more volatile than the cannabinoid-rich fraction it can be removed in an initial extraction step at a lower temperature. The temperature may then be increased in order to volatilise the cannabinoid-rich fraction. The temperature required to preferentially volatilise terpenes may vary depending on the nature of the starting *cannabis* plant material, but can be readily determined by experiment as would be apparent to one skilled in the art. By way of example, for "high CBD" material a temperature in the range 125-150° C. is observed to result in preferential volatilization of a terpene-rich fraction. Whereas, for "high THC" material a temperature in the range 60-90° C. is required. In order to optimise condensation of the volatile terpene fraction the conditions used for condensation may also be varied, in addition to the temperature of the heated gas used to volatilize this component.

Once the terpene-rich fraction has been removed, the temperature of the hot gas may be increased in order to volatilise the cannabinoid-rich fraction. Again, the optimum temperature for extraction of the desired cannabinoid components may be determined by experiment. By way of example, for "high CBD" *cannabis* plants a temperature in the range 175-200° C. is preferred. Whereas, for "high THC" *cannabis* plants a temperature in the range 130-175° C. may be suitable. At 200° C. a cannabinoid-rich fraction may still be collected but thermal degradation of $\Delta^9$-THC is increased. Hence it is preferred to use a lower temperature.

Thus, the skilled reader will appreciate that by simple empirical variation of the conditions used for volatilisation and condensation it is possible to optimise separation of the terpene-rich and cannabinoid-rich fractions.

A still further advantage of the process of the invention in relation to the preparation of cannabinoid-rich fractions from *cannabis* plants is that the extracts prepared using the process contain cannabinoid components in approximately the same ratio as present in the starting material. Thus, substantially no fractionation of the cannabinoids is observed.

In the context of this application the terms "*cannabis*", "*cannabis* plant material" or "*cannabis* biomass" refer to whole *cannabis* plants and also parts thereof which contain the principal medically active constituents, for example the aerial parts of the plant or isolated leaves and/or flowering heads. The terms "*cannabis*" and "*cannabis* biomass" encompass freshly harvested plant material, and also plant material which has been subjected to a pre-treatment step such as, for example, material which has been dried. This includes *cannabis* material which has been allowed to air dry after harvesting.

It is convenient to process high CBD and high THC *cannabis* chemovars separately to produce extracts rich in either THC or CBD from which mixtures containing defined proportions of THC and CBD can be made in the preparation of pharmaceutical formulations. Procedures described in the following examples with reference to one particular chemovar may be applied *mutatis mutandis* for any other *cannabis* chemovar.

In a further embodiment of the invention the principle of extraction with a heated gas may be utilised in a two-stage process for the preparation of extracts from plant materials which involves first preparing a primary solvent extract from the plant material.

As discussed previously, it is known to make an extract from plant material by percolation or maceration with a solvent and to fractionate the extract by concentration or various processes which have been described in the scientific literature for reducing extracts to a powder. However, botanical extracts prepared using such processes generally contain a variable, but usually considerable, proportion of inactive material or ballast which renders the extracts generally intractable as starting materials for pharmaceutical preparations.

The inventors have now observed that primary solvent extracts of natural products, such as plant material, may be further purified by extraction with a heated gas, resulting in removal of a substantial proportion of the inactive ballast.

Therefore, in accordance with a second aspect of the invention there is provided a process for preparing an extract from a natural product which comprises:

providing a primary solvent extract of the natural product;
contacting the primary solvent extract with a heated gas thereby volatilising one or more
constituents of the primary solvent extract to form a vapour;
condensing the vapour; and
collecting the condensate in one or more fractions.

This process (referred to hereinafter as the "solvent extract purification" process) may be used to prepare a "purified" extract starting from a primary extract of a plant material. The term "purified extract" refers to an extract which retains one or more desirable constituents from the starting primary extract but contains a lower amount of other, undesirable constituents. In a preferred embodiment the solvent extract purification process may be used to prepare a purified extract which retains pharmacologically active constituents from the primary extract whilst removing unwanted ballast.

The primary extract used as the starting material for the solvent extract purification process may be essentially any solvent extract of a plant material such as, for example, *cannabis* plant material. Extracts prepared with alcohols such as, for example, ethanol, methanol, isopropanol or industrial methylated spirit are particular suitable. Another suitable solvent is acetone. Extracts prepared by extraction with supercritical $CO_2$ may also be used.

Solvent extracts prepared with alcohols may be dried down by evaporation of the solvent to yield a soft extract (as defined in the British Pharmacopoeia) and then re-dissolved in the same or a different solvent prior to contact with the heated gas. This will allow for adjustment of the concentration and viscosity of the extract prior to contact with the heated gas. The term "primary solvent extract" as used herein is therefore to be construed as encompassing extracts which have been dried down and re-dissolved.

In the case of *cannabis*, it is preferred to use a primary extract prepared using a mixture of alcohol and water. The use of such mixtures reduces the lipophilicity of the solvent system and leads to proportionately greater extraction of cannabinoid acids. The extraction of cannabinoid acids in progressively more dilute alcohols is observed to be increased at high pH.

The primary solvent extract may be prepared using conventional techniques known in the art such as, for example, maceration, percolation and reflux (Soxhlet) extraction. The solvent used for primary extraction may be chosen according to the known solubility characteristics of the active ingredients or their precursors in the plant material. Since it will be subject to a further extraction step the primary solvent extract may be a fairly crude extract.

In a preferred embodiment the step of contacting the contacting the primary solvent extract with a heated gas comprises loading the primary solvent extract onto a matrix of inert, porous material and circulating a heated gas through the matrix, thereby volatilising one or more constituents of the primary solvent extract to form a vapour.

The primary solvent extract is loaded onto a matrix of inert, porous material which provides a large surface area for contact between the primary extract and the heated gas. Suitable inert matrix materials include glass wool, which may be coated (e.g. silanised) to modify its surface retentiveness. In one embodiment the glass wool may be in the form of a pre-formed mat of spun glass (Rockwool), rolled to form a cylinder. Other suitable inert, porous matrix materials include, for example, glass beads or short sections of glass tube, borosilicate glass or pharmaceutical grade stainless steel. For convenience, the matrix material maybe packed into a column formed of an inert material, such as borosilicate glass. A suitable apparatus is described below and illustrated in the accompanying examples.

Heated gas is then circulated through the matrix material in order to volatilise one or more constituents of the primary solvent extract, forming a vapour. The temperature of the heated gas will vary depending on the nature of the component(s) which it is desired to volatilise from the primary extract. The temperature of the heated gas may also be varied over time. For example, depending on the composition of the primary extract it may be desirable to circulate heated gas at a first temperature in order to volatilise unwanted components of the primary extract and then to adjust the temperature to a second, higher temperature to volatilise desirable components of the primary extract.

Suitable "heated gases" for use in the process include hot air, inert gas and dry steam, alone or in combination. The most preferred gases are inert gases, dry steam and mixtures thereof. Mixtures of inert gas and dry steam are referred to as anaerobic gas mixtures. By excluding air, through use of an anaerobic gas mixture, oxidative degradation of the extract is reduced or avoided. Examples of suitable anaerobic gas mixtures are dry steam mixed with one or more of nitrogen, carbon dioxide, helium or argon.

Oxidation can be further reduced by use of a reducing gas mixture. By "reducing gas mixture" is meant an anaerobic gas mixture containing a proportion of a volatile antioxidant, or means for generating an antioxidant in situ during the extraction process.

The vapour produced by volatilisation of constituents of the primary solvent extract is condensed- and collected. The condensate may be a homogeneous liquid but may, depending on the nature of the starting material, form a mixture of oily and aqueous components. In the latter case, the apparatus used for carrying out the process may further include means for collecting the condensate in two or more separate fractions.

The primary solvent extract may be subjected to a chemical treatment prior to loading onto the inert matrix. In one embodiment, the extract may be treated to adjust pH, for example by addition of an acid or an alkali. Where the active constituent which it is desired to isolate from the plant material is an alkaloid salt or other adduct, the alkaloid may be rendered volatile by adjustment of pH. Subsequent treatment with heated gas at a temperature which volatilises the alkaloid may then result in a product which is substantially free of inactive ballast.

Surprisingly, it has been found that use of the solvent extract purification process can speed the conversion of inactive constituents of plant materials into compounds which are biologically active and can be separated in high purity. For example, as described above the cannabinoids which are the principal active constituents of *cannabis* plants, particularly *Cannabis saliva* and *Cannabis indica*, are present in the plant as the corresponding carboxylic acids. With use of the solvent extract purification process it is possible to prepare a purified *cannabis* extract, containing a high proportion of free cannabinoids, starting from a primary solvent extract. There is no need to perform a separate decarboxylation step before preparation of the primary solvent extract. A primary extract is simply prepared from *cannabis* plant material, loaded onto matrix material and treated with heated gas. Circulation of the heated gas through the primary solvent extract results in decarboxylation of cannabinoid acids and volatilisation of free cannabinoids in a single process step. The vapour comprising the free cannabinoids is collected by condensation. The resulting condensate is substantially free of inactive ballast and suitable for formulation into pharmaceutical dosage forms.

The temperature of the heated gas used in the processing of *cannabis* extract must be sufficient both to effect decarboxylation of cannabinoid acids and to volatilise the free cannabinoids. Temperatures in the range of 105°-350° C., and preferably 125°-218° C. are suitable for this purpose. Decarboxylation of cannabinoid acids is a function of time and temperature, thus at lower temperatures a longer period of time will be taken for complete decarboxylation of a given amount of cannabinoid acid.

According to a further aspect of the invention there is provided an apparatus for extracting useful substances from natural products, the apparatus comprising a receptacle for receiving the natural product, a blower to blow gas through the receptacle, a heater for heating the gas blown through the receptacle, a condenser to condense the vapour from the receptacle, and a means for collecting the useful substances in the condensed liquid.

In one embodiment, the receptacle is a drum rotatably mounted in a housing to rotate about an axis. Alternatively, the receptacle comprises a stack of baskets each having a perforated base which allow the passage of gas, but substantially not the natural product.

Examples of apparatus according to the invention will now be described with reference to FIGS. 1 to 4.

The primary component of the apparatus shown in FIGS. 1 to 3 is a rotatable drum 1 which is mounted in a housing 2. The drum 1 is mounted for rotation about an axis 3. The drum 1 has an octagonal cross-section in a plane perpendicular to the axis 3 as shown in FIG. 3. Each side of the drum 1 comprises a mesh sheet 4 having a wire diameter of 0.16 to 0.28 mm and an open area of 45 to 39% which is designed to retain particles of 1×2 mm. The front of the drum is closed by a plate 4A bolted in place and held by a plurality of wing nuts 4B.

The drum 1 is driven by a variable speed geared motor 5 coupled via torque coupling 6 to a rotatable shaft 7 supported on a pair of bearings 8. The rotatable shaft 7 enters the housing 2 through a lip seal 9 and has a key groove 10 which engages with a complementary key rib in the drum so as to transmit rotational movement thereto. A drain part 2A is provided in the bottom of the housing 2 to allow any accumulated liquid in the housing to be drained.

The housing 2 is open at the end opposite to the motor 5. This opening is selectively closable by a hinged door 11 and seals by virtue of an annular seal 12. The door 11 is provided with an inspection window 13 as shown in FIG. 1. The loading and unloading of the product is accomplished by removing the wing nuts 4B and hence plate 4A, removing any spent product, replacing it with fresh product and replacing the plate 4A and wing nuts 4B. To clear the equipment between batches, the entire drum 4 may be removed from the housing 2, by unfastening the drum from the shaft 7. The drum 4 can then be cleaned and reused. It will be quicker, however, to have a second drum which is pre-filled with product and can be used in place of the first drum while the first drum is cleaned.

Hot gas is blown into the housing 2 through an air knife 14 supplied from hot gas supply nozzle 15. The air knife 14 provides a long thin air duct extending parallel to axis 3 for substantially the entire length of the drum 1. The air knife 14 is positioned immediately adjacent to the drum 1, and is directed generally towards the centre of the drum, but not directly at the axis 13.

In use, a natural product such as medicinal *cannabis* is coarsely chopped and loaded into the drum 1 as described above. The *cannabis* may be in its "as grown" state, or may have been subjected to a pre-treatment step, for example a drying step. Typically 5 kg of *cannabis* will be loaded into the drum. A gas such as nitrogen is injected through a duct 20 and is blown by a sealed fan 21 through a heater 22, where it is heated to a temperature of around 200° C., via hot gas supply duct 15 and into the housing 2 through the air knife 14. Simultaneously with the gas injection, the drum 1 is rotated by the motor 5 at a rate of between 0.1 and 60 r.p.m. This rotary motion causes the product to fall through the space in the drum, while the hot gas flowing through the air knife 14 keeps the product away from the walls of the drum. The hot gas causes the active substances within the product to vaporise and the hot vapour leaves the housing 2 through an outlet 16. A filter 17 traps large particles entrained in the vapour.

The vapour then travels along discharge duct 23 to a cyclone separator 24 which separates out smaller particles from the vapour. It is possible that either the filter 17 or the cyclone separator 24 will be sufficient on its own to separate out all of the particulates from the vapour.

The vapour which is now substantially free of solids leaves the cyclone separator 24 through cyclone outlet duct 25 and passes through the fan 21. Temperature can be equilibrated and vapour can be recirculated by closure of motorised butterfly valves 26 and 26A. Vapour passes through a condenser 28. The condenser 28 is cooled by a water jacket 29 to which water is supplied through duct 30 and returned through duct 31. The distillate leaving the condenser 28 containing the active substance accumulates in collector 32. The vapour may be vented via a steam trap 33 or may be recirculated via a scrubber 34 or an iced chiller 35 along return line 36 where it joins the recirculating hot gas stream upstream of the heater 22. The scrubber 34 may be a glass wool or charcoal scrubber and is designed to remove the smell from the vapour. A preferred type of scrubber contains C18 reverse-phase chromatography support in granular, permeable form which effectively absorbs any particles of lipid-soluble material. The chiller 35 is provided to chill the vapour to condense terpenes. A typical design of chiller utilises a freezing mixture of acetone and solid carbon dioxide giving a temperature of −65-70° C. to condense remaining traces of vapour.

Prior to use, and before any natural product is placed in the drum, the apparatus is flushed with nitrogen which is then vented through vent 36 prior to heating.

A dry steam inlet 38 may also be provided to give an anaerobic alternative to nitrogen. Dry steam allows vaporisation to occur at a lower temperature than with nitrogen.

In practice, the apparatus upstream of the condenser (i.e. the housing 1, heater 22 and cyclone 23) will be housed in a common insulated container to avoid expensive lagging of individual components.

An alternative apparatus is shown in FIG. 4. As with the example in FIG. 1, the apparatus in FIG. 4 is also designed to force a stream of heated gas through a perforated container holding a supply of natural products such as medicinal *cannabis*.

The apparatus of FIG. 4 comprises a sealed and insulated housing 40 into which gas flows through a heated gas inlet 41. This inlet 41 passes through a heat exchanger 42 such that the cold incoming gas is heated with hot outgoing gas as will be described below. The interior of the housing 4 is heated by an electric heater 43 such that the preheated gas entering the housing 40 is heated further. A fan (not shown) is provided to drive the air into the housing 40. A double acting pump 44 is positioned within the housing 40. This consists of a piston 45 which reciprocates within a cylinder 46. The pump has a first inlet valve 47 which allows air into the top of the cylinder during the piston downstroke and a second inlet 48 which allows air into the bottom of the cylinder during the piston upstroke. A first outlet 49 lets air out of the top of the cylinder during the piston upstroke while a second outlet 50 allows air out of the cylinder during piston downstroke. Flow through each of the inlet and outlet valves is controlled by a one-way flap valve. Thus, the double acting pump 44 provides a cyclic varying output of hot gas which is conveyed via a duct to a carousel assembly 51.

The carousel assembly 51 comprises an upper disk 52 and an axially aligned lower disk 53, both of which are connected to a spindle 54 which passes through their centres. The spindle is rotatable so as to rotate the upper 52 and lower 53 disks. Each of the upper 52 and lower 53 disks passes through the wall of the housing 40 and a seal 55 is provided at each interface. Each disk 52, 53 is provided with a number, preferably two or more and typically six, of circular orifices 56, each of which is sized to receive a basket 57. Baskets 57 have a mesh base 57A and solid walls 57B with a recess in the rim to retain a silicone rubber ring washer 65. The baskets nest together and the ring washer ensures that gas passes through the baskets and their content and not around them. The baskets 57 are loaded by upper disk 52 into a column 58. The first loaded basket drops down the column 58 and is supported above a series of baffles 59 at the lower end of the column 58. Further baskets 57 are then-loaded on top of this.

Initially, a full stack of baskets is inserted as shown. The double acting pump 44 is then operated to push hot gas upwardly through the column. Gas expelled from the top of the column passes through heat exchangers to pre-heat the incoming gas. The flow of hot gas up column 58 vaporises the active ingredient as in the previous example, and the expelled vapour is treated as previously described with reference to FIG. 1, namely be being passed through a separator such as a filter or cyclonic separator into a condenser 60. Also shown in this example is an optional secondary condenser 61 and exhaust pump 62. The condenser 60 has an upper outlet 63 and lower outlet 64 to allow withdrawal of different fractions of the condensate should it separate into layers. Such an arrangement may also be employed with the condenser of FIG. 1.

As the process progresses, the product in the lowermost basket 57 will be exhausted at a faster rate than the product in successively higher baskets because it encounters the freshest gas, i.e. a counter current flow arrangement is operated. After a certain time, or once the level of active substances being collected has dropped below a certain level, the lowermost basket is removed by rotation of the lower disk 53 which takes the basket outside the housing 40 where it can be removed for disposal. A fresh basket is pre-loaded into an orifice 56 in the uppermost basket 52 outside the housing 40. As the lowermost basket is removed, the upper disk is rotated bringing the fresh basket into a location at the top of the column 58. A reciprocable plunger 66 is then deployed to push the new basket out of the hole 56 in the upper disk 52 and to ensure that all of the baskets 57 are pushed down the column 58 so that the lowermost basket rests on the baffles 59.

After a suitable interval, this process is repeated so that fresh baskets of product are periodically added to the top of the column and gradually progress down the column until they are removed from the bottom.

FIG. 5. shows a small scale laboratory apparatus suitable for carrying out the solvent extract purification extraction process. This apparatus may be assembled from commercially available proprietary laboratory glassware. The apparatus comprises a hollow cylindrical column 69 formed of borosilicate glass or similar inert material. The column is packed with an inert matrix material 70, for example glass wool, glass beads or short sections of glass tube. A heating mantle 71 is fitted around cylindrical column 69 and provides heat and insulation to maintain the cylinder at its operating temperature. In other embodiments the column may be contained within an oven which is maintained at a specific temperature controlled by a thermostat.

The apparatus further includes a re-circulation pipe 72 fitted with a valve 73 and sampling port 74 and a outlet pipe 75 also fitted with a valve 76 which feeds into the condenser assembly. The condenser assembly of the apparatus shown in FIG. 5. includes two condensers 77, 78 arranged in series.

Heated gas is introduced into the device via an inlet port 79 at the bottom of the cylindrical column. A stream of heated gas may be conveniently provided using an electrical heater/blower device.

The re-circulation pipe 72 operates to re-circulate gases though the column when valve 73 is in the open position and valve 76 is in the closed position. When valve 73 is closed and valve 76 is open gases exit the cylinder via outlet pipe 75 and are delivered to the condenser assembly. Condensate exiting the condenser assembly is collected in a receiving vessel (not shown).

The apparatus further includes a thermistor 80 and flow gauge 81 for monitoring the temperature and flow of gas in the apparatus.

The invention will be further understood with reference to the following, non-limiting, experimental examples.

Example 1—Extraction with Ethanol

The following method of extraction is essentially that described in major pharmacopoeias such as the British Pharmacopoeia, European Pharmacopoeia and United States Pharmacopoeia. It is included here to provide a datum point for comparison of the extracts produced by methods illustrated in later examples. The method can be used *mutatis mutandis* to prepare total extracts of other chemovars of *cannabis*.

High $\Delta^8$-tetrahydrocannabinol (THC) *cannabis* chemovar, coarsely chopped in a cutter mill, is decarboxylated by heating at 145° C. for one hour. A quantity of 100 g of decarboxylated herb is packed into a cylindrical vessel fitted with a frit (mesh screen) to retain solid particles and a tap in the exit tube. A second frit is placed over chopped *cannabis* to prevent splashing. The *cannabis* is moistened with 90% ethanol; a further quantity of ethanol is added to completely saturate the plant material and allowed to stand for 24 hours. The tap is opened and the percolate is collected. A drip feed of ethanol is fixed up above the *cannabis* so that the mass remains saturated with ethanol. Percolation is continued, reserving the percolate until the percolate is no longer darkly coloured, and when 1 ml of percolate tested by HPLC shows less than the equivalent of 0.1 mg of THC per ml. The presence of cannabinoid is revealed by adding 0.1 ml of Fast Blue Test Solution is added to 1 ml percolate. Cannabinoids produce characteristic colours (orange—CBD; pink—THC; and purple—CBD) in this test.

The reserved percolate is then evaporated to dryness in a rotary evaporator and assayed by HPLC. Essential details of the assay method are given below. A person skilled in the art will appreciate that other configurations of column, mobile phase and operating conditions having the required discrimination and accuracy are suitable for the purposes of estimating cannabinoid content.

Extract: Typically 0.1 g of ground plant tissue/5 ml of chloroform, methanol
1.9 g
Columns: S3 ODS2 3×0.46 cm pre-column and Discovery C8 15×0.46 cm analytical column
Mobile Phase: 0.25% w/v acetic acid in Water:Methanol: Acetonitrile 6:7:16 (by volume)
Flow Rate: 1 ml/min
Detection: UV at 220 nm
Injection volume: 2 µl From Table 1 it can be seen that the extract so produced consists of THC principally, but there is also present some of the carboxylic acid (THCA), a little CBD, some CBDA and cannabinol. The remainder of the extract consists of ballast. Table 1 also gives the analysis of the extract produced from the high CBD chemovar using the method described above and shows that there are significant amounts of ballast present in the dry extracts. The product is a dark oleoresin; the dark brown colour indicating that there is considerable oxidation of plant pigments. The method can be used to produce an extract from the high CBD chemovar by substitution of the appropriate plant mass.

Ethanol extraction may be optimised by varying pH and/or strength of the ethanol solvent. Surprisingly it has been found that at high pH values, the carboxylic acids corresponding to cannabinoids are soluble in lower concentrations of ethanol/water, and that under these conditions there is more complete extraction of total cannabinoid content as shown by gravimetric determination.

Example 2—Extraction with Supercritical Carbon Dioxide 100 g of *cannabis* (high CBD chemovar) are coarsely chopped in a Hobart cutter mill then decarboxylated as described in Example 1. Plant mass is packed, tamping down between successive layers, into the cavity of a supercritical fluid extraction apparatus. The mass is further compacted by axial pressure and frits are installed at either end of the *cannabis* mass. Carbon dioxide at a pressure of 100 bar and a temperature of 32° C. is admitted to the apparatus and extraction continued for 4 hours. At the end of this time eluate is vented through a pressure reduction system and the extract emerging at atmospheric pressure is collected in a glass vessel as a yellow/brown oil.

The distillate is dissolved in dehydrated ethanol and cooled to a temperature of −20° C.±1° C. for 24 hours and the waxy material removed by filtration. This process, known as "winterisation", is used in the oil industry to de-wax oils, but only removes a percentage of lipid material in extracts of *cannabis* (Table 1).

From Table 1 it can be seen that the product produced by this process is a yellow/brown oil which is lighter in colour than that produced by ethanolic extraction but the extract still contains significant quantities of carotenoid pigments. It also contains significant amounts of cannabinol which is regarded by some authorities as a degradation product of THC and CBD.

Example 3—Extraction with Heated Gas (Nitrogen)

Five kilos of coarsely chopped medicinal *cannabis* was loaded into the drum of an apparatus of the type shown in FIG. 1. Distillation of cannabinoids was effected with the use of pharmaceutical, quality nitrogen at a temperature between 175° C. and 250° C., which is below the temperature at which plant material chars or pyrolyses.

Example 4—Extraction with Heated Gas (Reducing Steam)

Using apparatus of the type illustrated in FIG. 1, 5 kg of freshly harvested *cannabis* was placed into the drum. The *cannabis* flowering heads and leaves were separated from stalk using a serrated comb with sharpened tines. The apparatus was equilibrated to a temperature of 110° C. and steam was introduced at 150° C. while the drum was set to rotate. A solution of sodium metabisulphite (10%) is introduced into the flow of steam in a quantity sufficient to give 10-500 parts of sulphur dioxide per million parts of wet biomass. When mixed with wet biomass, sodium metabisulphite reacts to produce sulphur dioxide which provides an antioxidant environment in which the extraction can be carried out. Oxidation of the extract is thereby minimised.

Vapour leaving the chamber was condensed and produced a mixture of oil and aqueous layer. The volatile oil so produced is useful as a component of medicinal flavouring and perfumery products. The collecting vessel was fitted with two taps, one at the lowest point and the other at a point on the wall of the glass container. After separation it is possible to draw off the saturated aqueous layer which contains considerable amounts of terpenes and other odiferous principles; the oily cannabinoid-rich fraction is discharged through the upper tap. By controlling the temperature of the condenser and the collection vessel it is possible to keep both aqueous and oily layers in non-viscous, liquid form for ease of handling.

It is apparent by observation of the oil level in the condenser when distillation of this fraction is substantially complete. At this point the contents of the condenser are removed. Steam was replaced with nitrogen and the temperature raised to 218° C. The receptacle for condensed liquor was replaced and the temperature in the reactor increased to 218° C. The vapour now produced was condensed and collected, as follows.

The vapour is admitted to a condenser which is cooled with water at a temperature of 50° C. Condensed material is still fluid at this temperature and may be collected in a suitable receptacle.

Vapour leaving the condenser may be passed through a cold finger chilled with carbon dioxide and acetone coolant which condenses valuable components remaining in the vapour.

The results obtained may be summarised as follows:
125° C./200° C. (FIG. 6.)
The low temperature phase produces no significant volatilisation of any components (during the time period of this study). The higher temperature phase produces significant volatilisation of cannabinoid which is collected on the cold trap, but the volatile terpene fraction is not condensed and is lost from the system.
150° C./200° C. (FIG. 7.)
The low temperature phase produces significant volatilisation of both terpene fraction and cannabinoid, both of which

TABLE 1

Characteristics of Extract of Cannabis

| Method of Extraction | Chemovar | Appearance of Extract | THC | THC | CBD | CBDA | CBN | Ballast (after Winterisation |
|---|---|---|---|---|---|---|---|---|
| 90% ethanol (Example 1) | G1 | Dark brown | 50 | 4 | 1 | 2 | 2 | 40 |
| 90% ethanol (Example 1) | G5 | Dark green/brown | 3 | 0.5 | 55 | 5 | 2 | 34 |
| SCCO$_2$ (Example 2) | G1 | Yellow/green/brown olecresin | 60 | 6 | 1.5 | 2.5 | 2 | ( ) |
| SCCO$_2$ (Example 2) | G5 | Yellow/Green/brown | 4 | 0.5 | 54 | 4 | 2 | ( ) |
| Distilled (Example 4) | G1 | Light Yellow | 98 | trace | 2.5 | trace | 0.5 | trace |
| Distilled (Example 4) | G5 | Light yellow solid | 1.5 | trace | 98 | trace | 0.5 | trace |

G1 = "high THC" Chemovar
G5 = "high CBD" Chemovar

Example 5—Heated Gas Extraction from High CBD Cannabis Chemovar

The following studies were carried out using a pilot-scale version of the apparatus of FIG. 1. The apparatus can be run continuously and accepts a charge of 50 g botanical raw material, which is heated for approximately 15 mins.

The starting botanical raw material was a high CBD cannabis chemovar (designated G5) containing more than 90% of total cannabinoid as CBD and its precursors. Extraction was carried out by contacting the botanical raw material with forced hot air flow at various selected temperatures. An inert atmosphere of nitrogen could be substituted for the flow of air, for example if it is necessary to prevent oxidation of the minor cannabinoid component THC to CBN. Volatilised components were condensed by means of a "cold finger" filled with a salt/ice freezing mixture.

A series of experiments were carried out to determine the temperature profile required to resolve the cannabinoids, consisting predominantly of CBD, from the unwanted terpene fraction (volatile oil fraction with gas chromatogram R.T.'s in the region 14 min-21 min). A basic approach of a lower temperature initial phase, to volatilise terpenes and other essential oil components, followed by a higher temperature phase to volatilise the higher boiling point cannabinoids was adopted. FIGS. 6-8, which show gas chromatography analysis of the condensed factions collected following volatilisation at each of the chosen temperatures, plus GC analysis of starting material and spent herb. GC results obtained for the starting material (botanical raw material) and spent herb after each run are based on the analysis of total solvent extractable fraction. This is representative of the qualitative composition of the herbal material before and after hot gas extraction.

are collected on the cold trap to produce a complex mixed fraction. The most abundant peak in the terpene region of the GC trace is a new compound not present in the starting material, which may represent an oxidised terpene product. The high temperature phase results in a cannabinoid-rich fraction containing little terpene.
175° C./200° C. (FIG. 8.)
The low temperature phase produces cannabinoid enriched rich fraction essentially free of terpenes. The high temperature phase produces a fraction of comparable composition to that obtained during the low temperature phase.

The employment of a two-stage temperature profile can thus result in successful separation of cannabinoid from the terpene fraction, resulting in a cannabinoid enriched extract. Furthermore, it can be derived from these results that a single-stage temperature profile at a temperature of 175° C.-200° C. will also result in the production of a cannabinoid-enriched fraction substantially free of terpenes (see FIG. 6. 200° C. step, and FIG. 8).

Decarboxylation during the vaporisation process appeared to be essentially quantitative, with only neutral cannabinoid and no acid detected in the condensed fractions. Both CBD principal cannabinoid and the THC minor cannabinoid were present in the volatilised extract in approximately the same ratio as detected in the herbal starting material, indicating that no fractionation of cannabinoids had occurred.

Comparison of the results shown in FIGS. 6 and 7 indicates that a temperature of above 125° C. but below 150° C. is required to preferentially volatilise terpenes in this system. Optimisation of the extraction temperature within this range may allow preferential volatilisation of a terpene fraction which can be condensed and collected fraction, substantially free of cannabinoids.

Example 6—Heated Gas Extraction from High THC *Cannabis* Chemovar

The following studies were carried out using a pilot-scale version of the apparatus of FIG. 1. The apparatus can be run continuously and accepts a charge of 50 g botanical raw material, which is heated for approximately 15 mins.

The starting botanical raw material was a high THC *cannabis* chemovar (designated G1) containing more than 95% of total cannabinoid as THC and its precursors. Extraction was carried out by contacting the botanical raw material with forced hot air flow at various selected temperatures. An inert atmosphere of nitrogen could be substituted for the flow of air, for example to prevent oxidation of the cannabinoid component THC to CBN. Volatilised components were condensed by means of a "cold finger" filled with a salt/ice freezing mixture.

A series of experiments were carried out to determine the temperature profile required to resolve the cannabinoids, consisting predominantly of THC, from the unwanted terpene fraction (volatile oil fraction with gas chromatogram R.T.'s in the region 14 min-21 min). Special considerations in the extraction of THC are to prevent/minimise thermo-oxidative degradation of THC to CBN and to prevent/minimise thermal isomerisation of $\Delta^9$-THC to $\Delta^8$-THC, whilst avoiding collection of terpenes with the cannabinoid fraction.

Figure 10:
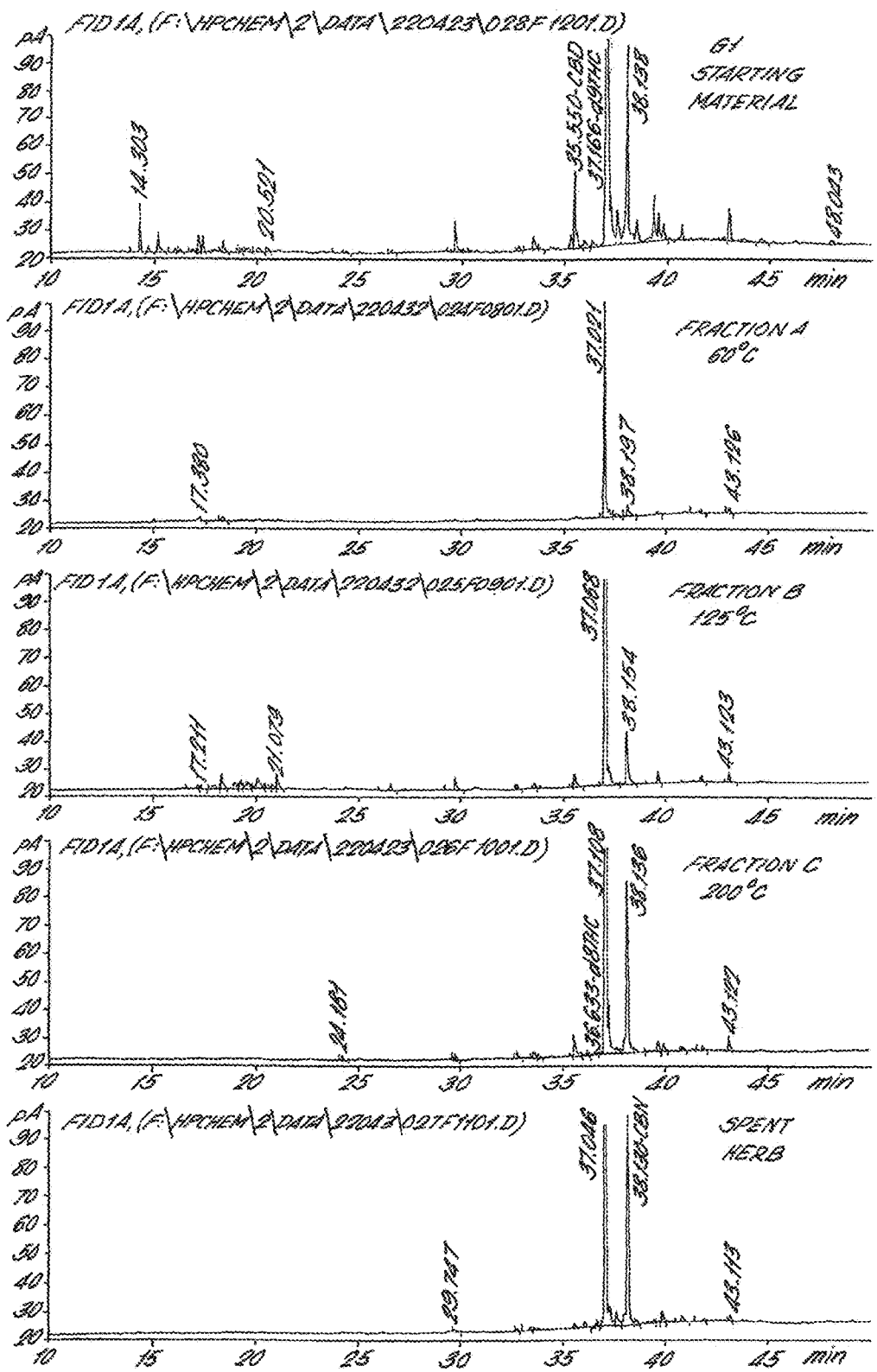

A basic approach of a lower temperature initial phase, to volatilise terpenes and other essential oil components, followed by a higher temperature phase to volatilise the higher boiling point cannabinoids, optionally with the inclusion of a third intermediate temperature phase, was adopted. FIGS. 9 and 10 show gas chromatography analysis of the condensed factions collected following volatilisation at each of the chosen temperatures, plus GC analysis of starting material and spent herb.

GC results obtained for the starting material (botanical raw material) and spent herb after each run are based on the analysis of total solvent extractable fraction. This is representative of the qualitative composition of the herbal material before and after hot gas extraction.

The results obtained are summarised in the following table:

TABLE 2

| SAMPLE | $\Delta^9$-THC | CBN | $\Delta^8$-THC | CBD | THC:CBN |
|---|---|---|---|---|---|
| BRM (G1) | 75.5% | 3.0% | 0.3% | 1.9% | 28:1 |
| Run 1 | | | | | |
| 125° C. | 51.5% | 6.2% | 0.4% | 1.2% | 8.3:1 |
| 200° C. | 63.3% | 12.8% | 0.5% | 1.1% | 4.9:1 |
| spent herb | 3.0% | 11.1% | 17.2% | N.D. | 0.3:1 |
| Run 2 | | | | | |
| 90° C. | 58.0% | 5.6% | 0.3% | 1.8% | 10.4:1 |
| 150° C. | 82.7% | 9.6% | 0.4% | 1.5% | 8.6:1 |
| 200° C. | 77.1% | 14.1% | 0.7% | 1.0% | 5.5:1 |
| spent herb | 54.0% | 25.7% | 2.6% | N.D. | 2.1:1 |
| Run 3 | | | | | |
| 60° C. | 78.6% | 7.2% | N.D. | N.D. | 10.9:1 |
| 125° C. | 75.3% | 6.0% | N.D. | 1.8% | 12.6:1 |
| 200° C. | 83.0% | 10.2% | 0.2% | 1.6% | 8.1:1 |
| spent herb | 64.1% | 23.7% | 0.6% | 0.9% | 2.7:1 |

The THC:CBN ratio is an indicator of the thermo-oxidative stress to which the material has been subject during the vaporisation process.

The results from run 3 indicate that a temperature of above 60° C. is required in order to volatilise terpenes. At a temperature of 90° C. (run 2) terpenes are volatilised, but only the less volatile terpenes are condensed. These results suggest that a temperature between 60° C. and 90° C. may be optimum for volatilisation and condensation of a separate terpene fraction.

The results from run 2 indicate that at 150° C. a cannabinoid-rich fraction is condensed, which is substantially free of terpenes. A similar profile is obtained at 200° C., however at this temperature the amount of $\Delta^8$-THC and CBN is increased, indicating thermal-oxidative degradation and thermal isomerisation of $\Delta^9$-THC. Similar results are seen in run 3, where the fraction obtained at 200° C. is free of terpenes but contains a higher proportion of $\Delta^8$-THC and CBN. It is therefore preferred to use a temperature which is as low as possible in order to minimise thermal-oxidative degradation and thermal isomerisation of $\Delta^9$-THC, whilst still resulting in a fraction which is substantially free of terpenes. A range of from 130° C. to 175° C. is preferred.

Example 7—Purification of an Ethanol Extract by Extraction with Heated Gas

High pH and low pH ethanolic solutions were prepared by adding 5 ml of m/l sodium hydroxide or hydrochloric acid solution to absolute ethanol and sufficient purified water to produce 100 ml of solvent. This quantity of solvent was used to percolate 10 g of *cannabis* herb, as described in Example 1.

Percolation of the *cannabis* herb was continued to exhaustion as described in Example 1 and evaporated to a soft extract (as defined in the British Pharmacopoeia). The extract was re-dissolved in ethanol to give a solution with a viscosity in the range 100-500,000 cps (preferably 50-150,000 cps using a Brookfield viscometer) and poured onto the cylindrical column of an apparatus of the type illustrated in FIG. 5. The column was constructed of borosilicate glass and packed with glass wool. Sufficient quantity of extract was added to coat but not saturate the column. Care was taken to ensure that the extract was retained within the pre-packed column.

The loaded column was assembled and connected to a condenser assembly and an electrical heater/blower. Air at a temperature of 60° C.-120° C. was blown through the cylinder and maintained at the same temperature. At this temperature volatile components consisting mainly of water, alcohols, and low boiling point terpenes are volatilised then condensed and collected in the receiver. When distillation of these low boiling components was substantially complete (indicated by a rise in temperature in the vapour leaving the column), the supply of gas was stopped and the receiver changed or emptied.

The temperature of the cylindrical column was increased to 218° C. and gas blown through the cylinder for 20 minutes. The gas was re-circulated through the cylinder with valve 76 closed and valve 73 opened. During this period cannabinoid acids are decarboxylated. Decarboxylation is substantially complete when a sample is taken from sampling port 74 shows that the free cannabinoid has reached a maximum level, measured by HPLC. At this point valve 76 was opened and valve 73 closed. Vapour was condensed in the condenser assembly and the condensed distillate collected. The distillate so produced consists of the total cannabinoids of the extract with very little cannabinoid acid, and is suitable for formulation into pharmaceutical dosage forms.

Example 8—Preparation of a Methanolic Extract

Total extracts of high THC and high CBD *cannabis* chemovars were prepared using ethanol as follows:

Biomass from each chemovar was separately extracted in a column with methanol at room temperature, and the pooled percolate was collected. Solvent was removed by evaporation in a rotary evaporator at a temperature not exceeding 43° C.

The invention claimed is:

1. A cannabinoid-rich extract which is substantially free of volatile terpenes and ballast, and has a high content of cannabidiol (CBD) and only trace amounts of tetrahydrocannabinolic acid (THCA) and cannabidiolic acid (CBDA), and wherein the majority of the cannabinoids are present in the decarboxylated neutral form.

2. The cannabinoid-rich extract as claimed in claim 1, wherein said extract has a profile by gas chromatographic analysis that comprises peaks as defined by retention times in one of the following sets of peaks:
   (1) 35.7±1 minute (CBD);
   (2) 24.1±1 minute, 35.9±1 minute (CBD), and 49.7±1 minute;
   (3) 32.1±1 minute, 35.7±1 minute (CBD), and 43.5±1 minute; or
   (4) 35.7±1 minute (CBD), and 45.8±1 minute.

3. The cannabinoid-rich extract as claimed in claim 1, wherein said extract has a profile by gas chromatographic analysis that comprises peaks as defined by the following retention times: 32.1±1 minute, 35.7±1 minute (CBD), and 43.5±1 minute.

4. The cannabinoid-rich extract as claimed in claim 1, wherein said extract comprises about 98% (w/w) cannabidiol (CBD), 1.5% (w/w) tetrahydrocannabinol (THC), 0.5% (w/w) cannabinol (CBN) and only trace amounts of ballast.

5. The cannabinoid-rich extract as claimed in claim 1, wherein said extract is substantially free of tetrahydrocannabinol (THC).

* * * * *